United States Patent [19]

Bakanowski

[11] Patent Number: 5,324,186

[45] Date of Patent: Jun. 28, 1994

[54] APPARATUS FOR MOLDING A DENTAL PROSTHESIS

[75] Inventor: Joseph T. Bakanowski, Reading, Pa.

[73] Assignee: Douglas R. Held, Wyomissing, Pa.; a part interest

[21] Appl. No.: 19,445

[22] Filed: Feb. 18, 1993

[51] Int. Cl.$^5$ .................. B29C 33/10; B29C 33/12; B29C 45/14; B29C 45/28

[52] U.S. Cl. .................. 425/116; 249/54; 249/95; 264/17; 425/192 R; 425/546; 425/556; 425/567; 425/569; 425/812; 425/DIG. 11

[58] Field of Search .................. 425/2, 116, 595, 546, 425/420, 192 R, 423, 812, DIG. 11, 556, 567, 571, 569; 249/54, 95; 264/17, 18

[56] References Cited

U.S. PATENT DOCUMENTS

| | | | |
|---|---|---|---|
| 786,279 | 4/1905 | Franklin | 425/178 |
| 1,353,942 | 9/1920 | Akin | 425/178 |
| 1,875,660 | 9/1932 | Rodin et al. | 425/178 |
| 2,341,991 | 2/1944 | Jackson | 425/178 |
| 2,409,783 | 10/1946 | Moskey | 264/20 |
| 2,428,094 | 9/1947 | Raymond | 249/54 |
| 2,790,998 | 5/1957 | Dimmer | 264/18 |
| 2,976,570 | 3/1961 | Ettenberg | 249/54 |
| 3,298,067 | 1/1967 | Tencate | 425/175 |
| 3,543,303 | 11/1970 | Sacchiero | 249/164 |
| 3,663,141 | 5/1972 | Alain et al. | 425/175 |
| 3,813,201 | 5/1974 | Frederick et al. | 249/141 |
| 4,359,435 | 11/1982 | Kogure | 264/40.5 |
| 4,365,783 | 12/1982 | Kesling | 249/54 |
| 5,066,213 | 11/1991 | Ferincz | 249/54 |
| 5,151,279 | 9/1992 | Kimura | 249/54 |
| 5,175,008 | 12/1992 | Ueno | 425/178 |

OTHER PUBLICATIONS

"Injection Packing of Acrylic Resin: An Improved Technique," J. Craigon et al., The Dental Technician Technical Supplement (1986) 39, 4, 4–9.

Brochure, "Superinjector," Valplast Corp., Long Island City, N.Y., 1 page.
Brochure, "Product Feature: Justi Miracleflask," American Tooth Industries, Oxnard, Calif., 2 pagess.
Brochure, "Flasks & Presses," Darby Dental Lab Supply, 2 pages.
Brochure, "Flexite," 1 page.
"Denture Processing by Injection Molding," Clinical Research Assoc. Newsletter, vol. 11, Iss. 7, Jul. 1987, 6 pages.
"Injection Molding of Plastics for Dentures," Walter J. Pryor, The Journal of the American Dental Assoc., vol. 29, Aug. 1, 1942, 9 pages.

Primary Examiner—Khanh Nguyen
Attorney, Agent, or Firm—Nies, Kurz, Bergert & Tamburro

[57] ABSTRACT

A molding flask structure for molding close tolerance articles, such as prosthetic dental devices. The flask structure includes upper and lower flask members that each include cup-recesses adapted to face each other to define therebetween a mold cavity when the flask members are connected together. Assembly of the flask members is effected by a plurality of connecting bolts to securely hold the flask members together. Vent passageways are provided in the flask members to extend from the mold cavity to permit excessive internal pressures to be relieved to the exterior of the flask member. A sprue opening defined by semi-cylindrical recesses in contacting faces of each of the flask members extends from the mold cavity to the exterior to permit the introduction of molding material into the mold cavity. The sprue opening is partially threaded and partially unthreaded. The flask members can be made of a plastic material which is transparent to microwaves, to permit the molding material within the mold cavity to be cured thermally either by microwaves or by direct application of external heat to the flask.

10 Claims, 3 Drawing Sheets

APPARATUS FOR MOLDING A DENTAL PROSTHESIS

BACKGROUND OF THE INVENTION

1. Field of the Invention

The present invention relates to a molding method and apparatus, and more particularly to an improved molding method and apparatus for investment-type molding of close-tolerance plastic articles, such as a dental prosthesis.

2. Description of the Related Art

Typically, a dental prosthesis, such as a full or partial denture, is prepared by forming the tooth-supporting and gum-contacting portion of the prosthesis in a closed mold cavity into which a plastic, denture base material is introduced. The replacement teeth are first properly positioned within the mold cavity, which is defined by two mold-cavity-defining mold portions, to assume the proper relative positions to replace the lost natural teeth when the prosthesis has been formed and is positioned within the mouth of the patient. The cavity-defining mold portions are separated and the material, which is often of a dough-like consistency, is positioned within the mold cavity. The mold portions are then pressed together, to compress the dough-like plastic material so that it flows to fill the mold cavity to unite with the teeth. The material is cured to form the desired prosthesis upon hardening of the plastic material.

Initially, a dentist takes an impression of the portion of the patient's mouth at which the prosthesis is intended to be positioned. The impression is in the form of a casting of plaster of paris, or other impression-defining material. When the impression material is removed from the patient's mouth and has become solidified it is packed with dental stone, which upon hardening conforms almost exactly in shape with that portion of the patient's mouth at which the finished prosthesis is to be positioned. The plaster of paris, or other impression material, is then separated from the dental stone impression.

The teeth that are to be a part of the finished prosthesis are then positioned in the appropriate place or places on the dental stone impression of the patient's mouth. The resulting stone impression and teeth are a duplicate of the patient's mouth, with replacement teeth in position. The stone impression accurately defines the surfaces of the patient's mouth and gums over which the prosthesis fits and on which it is supported when in use.

After the stone impression of the portion of the patient's mouth has been formed, a wax material is then applied to the surface of the stone impression in the desired thickness to define the thickness and outer shape of the finished prosthesis. The replacement teeth are then positioned on the wax pattern in the same position and in the same orientation that they would assume when part of the finished prosthesis. The stone impression and wax pattern are then placed in a suitable mold, and a complementary mold portion is provided by investment casting of plaster of paris over the surface of the prosthesis. Upon hardening of the plaster defining the complementary mold portion, the mold portion is separated from the impression material and the wax is removed by melting it and letting it flow from the respective mold portions. The result is a two-part mold that includes in one part the teeth to be incorporated into the prosthesis. The resulting mold cavity corresponds in shape and thickness with the shape and thickness of the final prosthesis.

Molding material is then placed between the two mold portions, which are then pressed together and held in a clamping fixture while the prosthetic material is undergoing a curing operation, such as by the application of heat. After curing the prosthesis is separated from the plaster mold portions, and is then trimmed, ground, and polished for ultimate use.

The prior art process hereinabove described most often utilizes a heat curable resin having the consistency of a dough. The dough is manually packed into the space between the upper and lower portions of the mold, and normally several trial packings are needed before the mold is finally properly packed and suitable for undergoing the curing operation. Such trial packings result in wasted molding material, and they involve repetitious and time consuming procedures.

It is an object of the present invention to eliminate the trial packing steps, with their consequent waste of material and waste of time.

It is another object of the present invention to provide a mold structure within which both investment material and the prosthesis material can be introduced to substantially eliminate processing errors.

It is a further object of the present invention to provide a mold member that is of light weight, and that is transparent to heat and microwaves for permitting curing of the molding material.

SUMMARY OF THE INVENTION

Briefly stated, in accordance with one aspect of the present invention, molding apparatus is provided for molding a dental prosthesis, the apparatus including a first mold member having a substantially planar end face and a cup-shaped recess in the end face to define a first mold cavity portion. The first mold member includes a portion of a substantially-cylindrical recess formed in the end face and extending from the mold cavity portion to define a part of an injection port passageway. A threaded opening extends through the mold member from the first mold cavity portion, and at least one vent channel extends outwardly from the mold cavity portion.

A second mold member includes a portion of a substantially-cylindrical recess formed in the end face and extending from the mold cavity portion to define a part of an injection port passageway. A threaded opening extends through the mold member from the first mold cavity portion, and at least one vent channel extends outwardly from the mold cavity portion.

The apparatus includes a clamping arrangement for tightly clamping the mold members together in contacting relationship across their planar end faces. Additionally, the mold members each carry cooperable orienting structure for positioning the mold members relative to each other to define a substantially cylindrical injection port when the mold members are in contacting relationship across their planar end faces.

DESCRIPTION OF THE PREFERRED EMBODIMENTS

Figure 1:
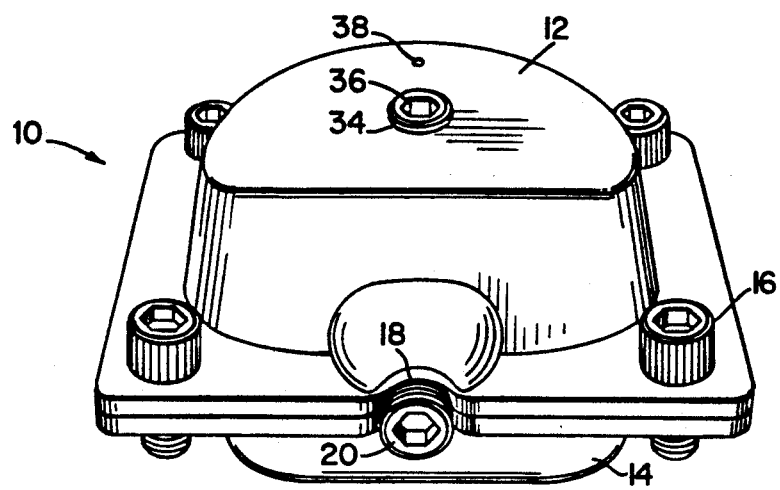
FIG. 1 is a top front perspective view of molding apparatus in accordance with the present invention, showing in assembled form an upper and a lower mold member that together define an interiorly positioned mold cavity.
Figures 2, 3:
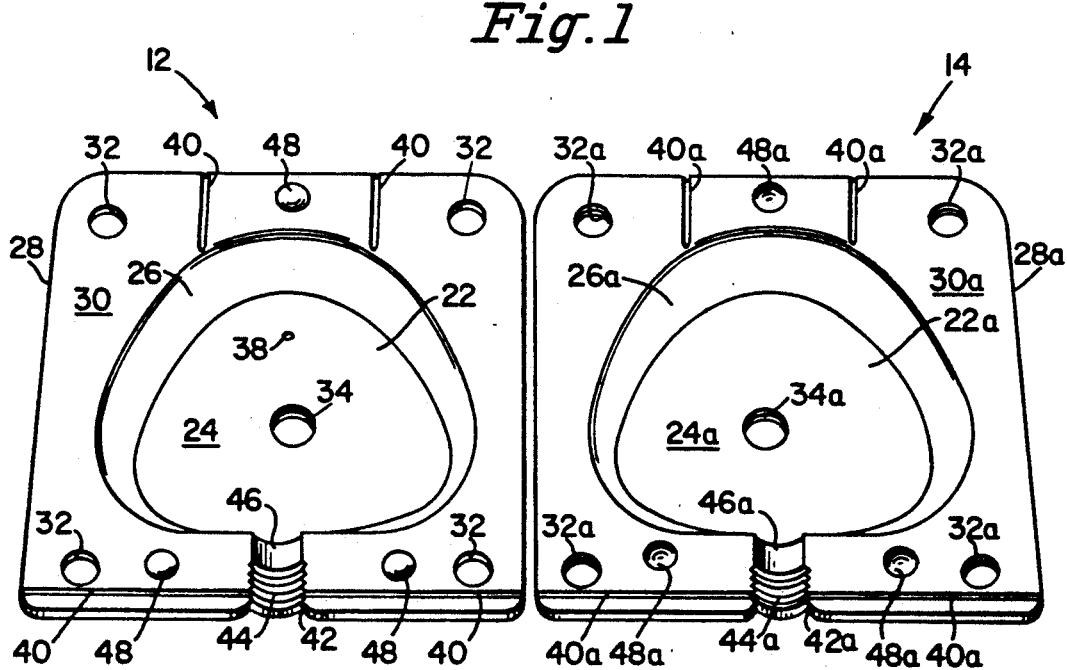
FIG. 2 is a bottom front perspective view of an upper mold member showing the interior portion of the upper mold member illustrated in FIG. 1.
FIG. 3 is a top front perspective view of a lower mold member showing the interior portion of the lower mold member illustrated in FIG. 1.

Referring now to the drawings, and particularly to FIGS. 1, 2, and 3 thereof, there is shown a molding flask 10 that includes an upper flask member 12 and a lower flask member 14. Flask members 12 and 14 are removably connected together by connecting bolts 16 to collectively define an interiorly positioned mold cavity, into which a mold-defining material is introduced, as will hereinafter be explained. A sprue opening 18 provides communication between the exterior of flask 10 and the mold cavity. As shown in FIG. 1, communication through sprue opening 18 is blocked by an externally threaded sprue closure screw 20 that is threadedly received within sprue opening 18.

Referring now to FIG. 2, upper flask member 12 is illustrated in inverted position, relative to the position in which it is illustrated in FIG. 1, to show the structure of the bottom and the interior of flask member 12. A cup-shaped, first cavity portion 22 is provided in flask member 12 and serves for receiving part of the mold-defining material. First cavity portion 22 is defined by a flat top wall 24 that can be of generally triangular form as shown, and preferably has rounded corners to facilitate removal from cavity portion 12 of mold-forming material. An upstanding wall 26 extends upwardly from the periphery of top wall 24, preferably in an outwardly diverging direction to provide mold draft, and terminates in an outwardly extending flange 28 having a flat end face 30. Flange 28 includes four through openings 32 that are disposed to define a rectangular array, as shown, and permit connection of upper flask member 12 with lower flask member 14 in a manner to be described hereinafter.

As shown in FIGS. 1 and 2, end wall 24 is flat, for purposes of convenience, and if desired it can be made dome-shaped, or any other shape consistent with the function of upper mold member 12 as a mold-cavity-defining element. A substantially centrally positioned threaded opening 34 extends through end wall 24 for removably receiving a correspondingly threaded closure screw 36. Opening 34 permits access to the interior mold cavity of flask 10 when upper and lower flask members 12 and 14 are in their assembled condition as shown in FIG. 1 to define the mold cavity. In addition to threaded opening 34, end wall 24 also includes a vent opening 38 that extends therethrough for venting gasses that otherwise would be trapped within the mold cavity defined by the respective flask members.

Lower flask member 14 is preferably of similar, complementary configuration to that of upper flask member 12, and corresponding parts are identified by the same reference numerals followed by an "a" to denote lower flask member parts. Lower flask member 14 is different from upper flask member 12 in that it does not include a vent opening in end wall 24a, as is provided in upper flask member 12, and instead of having four through openings 32 as provided in flange member 28 it includes four threaded openings 32a to threadedly receive connecting bolts 16.

In addition to the opposed, cup-shaped cavity portions 22, 22a formed in upper and lower flask members 12, 14, respectively, each flask member includes four vent channels 40, 40a, respectively. Vent channels 40, 40a are formed as depressions in the respective end faces 30, 30a of the flask members, and they define vent passageways that extend from the mold cavity when upper and lower flask members 12 and 14 are in assembled form, as shown in FIG. 1, to permit the escape of any trapped gasses from within the mold cavity defined by molding flask 10. Two vent channels extend laterally from sprue-opening-defining recesses 42, 42a, and two vent channels extend from cavity portions 22, 22a on the side opposite from sprue-defining recesses 42 and 42a. The vent channels also function as injection advisors, telling the operator that the mold is filled with the injected material when it appears at the outside of the vents.

Each of sprue-defining-recesses 42, 42a is of semicylindrical form and includes an outer, threaded portion 44, 44a, to threadedly receive closure screw 20, and a smooth-walled portion 46,46a, respectively. Sprue-defining-recesses 42, 42a each extend from the flask cavity to the exterior of the flask and define an outwardly-facing opening. Each recess includes an outer, threaded portion and an inner, unthreaded portion. When the flask members are assembled as shown in FIG. 1, recesses 42, 42a together define a cylindrical passageway that is partially threaded and partially unthreaded, the passageway permitting the introduction into the flask cavity of a molding material, as will be hereinafter described.

Each flask member also includes one element of a complementary, two-part flask member orientation arrangement, to enable the flask members to be properly oriented relative to each other when their end faces 30, 30a are placed in contacting relationship to define the assembled flask member illustrated in FIG. 1. As shown in FIGS. 2 and 3, upper flask member 12 includes three spaced, outwardly-extending, circular positioning buttons 48 that are arranged in a triangular array, and lower flask member 14 includes a similarly-arrayed plurality of circularly shaped recesses 48a for receiving the respective positioning buttons. Preferably, the complementary surfaces of buttons 48 and of recesses 48a are defined by spherical surfaces, although other surface forms can also be employed.

As shown in FIG. 1, the respective top and bottom flask members are joined together at surfaces 30 and 30a by four bolts 16 so that sprue-defining recesses 44 and 44a define a circular sprue 18. Connecting bolts 16 pass through apertures 32 formed in flange 28 of top flask member 12, so that the bolt heads bear against the upper surface of flange 28. The bolts are threadedly received in threaded apertures 32a formed in flange 28a of bottom flask member 14.

The flask members, as well as the connecting bolts, can advantageously be formed from a strong, high temperature material, such as metal or a fiber reinforced plastic, or the like. Preferably, the flask members are formed from a material that is capable of transmitting heat and of withstanding temperatures of up to about 450° F. Additionally, it is also preferred that plastic flask members be transparent to microwaves, to enable material within the flask cavity to be subjected to microwave radiation to heat the material for curing purposes. The minimum wall thickness of the flask members is preferably about 3/16 inch.

In making a prosthesis using the present invention, a wax pattern of the patient's mouth area at which the prosthesis is to be positioned is made in the usual manner. Initially, the upper and lower flask members 12 and 14 are not connected with each other, so that cup-shaped cavity portion 22a in lower flask member 14 is exposed and can be substantially filled with gypsum investment material. Before filling, a threaded closure screw, similar to closure screw 36, is threaded into opening 34a to close it to the passage of material. The wax model of the portion of the patient's mouth is then placed onto the investment material, and a release agent, of a type well known to those skilled in the art, is applied to the surface of the investment material to define a parting line.

The two flask members 12 and 14 are then assembled to provide a closed flask cavity, so that they are in the relative positions shown in FIG. 1. Connecting bolts 16 are tightened so that the end faces 30, 30a of the flask members are in tightly-contacting engagement. When assembled, the flask members define a sprue opening 18, that includes a threaded outer portion and a smooth walled inner portion. A sprue closure plug (not shown), such as a cork or a rubber plug of frustoconical form, is inserted into the sprue opening to close off the opening to flow of material. Preferably, the closure plug is of sufficient length to extend completely through threaded portion 44 and through smooth-walled portion 46 of the sprue opening to contact the wax impression, to provide a sprue passageway in the investment material that extends uninterruptedly from the exterior of flask assembly 10 to the wax impression. Threaded opening 34 in upper flask member 12 remains open and serves as the opening through which additional investment material is introduced into the flask cavity to surround that wax impression and to fill the cavity.

Figure 4:
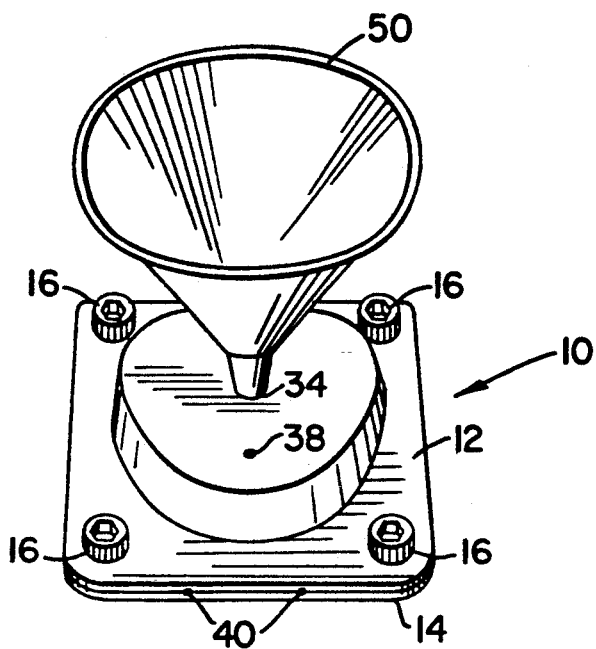
FIG. 4 is a top rear perspective view of the molding apparatus illustrated in FIG. 1, with an investment material feeding funnel shown in position for introducing investment material into the mold.
Figure 5:
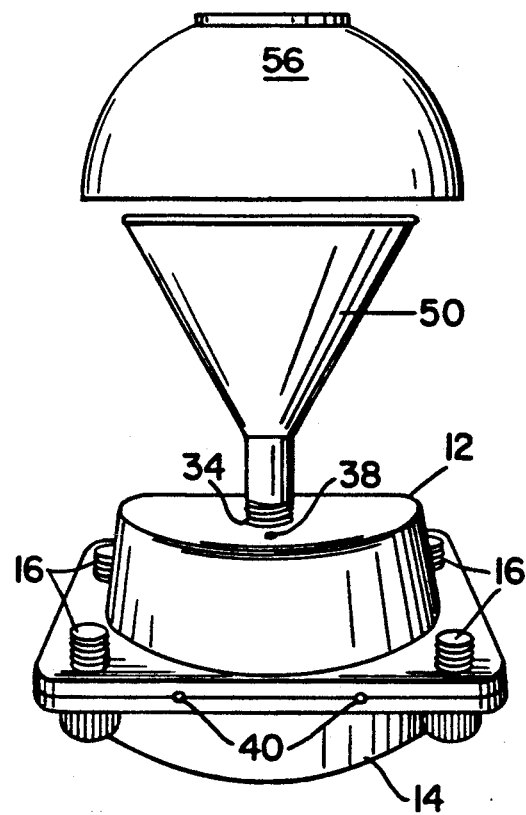
FIG. 5 is a top rear perspective view similar to that of FIG. 4, showing a funnel positioned on the mold and a packing pressure device overlying the funnel.

Introduction into the flask cavity of the additional investment material is effected by inserting the small end of a funnel 50, or other suitable feed device, as shown in FIG. 4, into opening 34 to guide the flow of the additional gypsum investment material into the flask cavity. The investment material is poured into the funnel so that it enters the flask cavity and completely surrounds and covers the wax model. The assembled flask 10 can advantageously be placed on a vibrator, to cause the investment material to freely flow into and fill the flask cavity. As an alternative to the gravity flow arrangement shown in FIG. 4, the investment material can be fed into the flask cavity under pressure, to assure complete filling of the flask cavity. In that connection, FIG. 5 shows one possible arrangement for applying pressure to the investment material after it has been introduced into the flask cavity. A cup-shaped plunger member 56 is positioned against the enlarged, upper end of funnel 50 to apply pressure to the investment material that is within funnel 50 to force the material into and to completely fill the flask cavity. Alternatively, the threaded opening 34a can be suitably connected with a source of vacuum to assist in filling the flask cavity with the investment material.

After the investment material has filled the flask cavity, funnel 50 is removed and a top flask closure plug 36 is threaded into position in opening 34, as shown in FIG. 1.

After allowing the investment material to solidify, the assembled flask 10 is warmed by placing it in hot water to soften the wax until the wax can flow. The sprue closure plug is removed and the melted wax is allowed to flow through the sprue opening. Upper and lower flask members 12 and 14 are then separated from each other by unscrewing connecting bolts 16, which exposes the investment mold halves that have separated along the parting line. Any remaining wax is then removed from the respective investment mold portions, and the resulting investment mold surfaces, that define the mold cavity for the prosthesis, are flushed and cleaned. After cleaning of the investment mold surfaces, a release agent is applied to the respective investment mold surfaces. The teeth to be carried by and to form part of the finished prosthesis are then positioned in the appropriate investment mold surface, after which the upper and lower flask members are then reassembled to once again assume the relative positions shown in FIG. 1, to thereby define an interior investment mold cavity that corresponds with the form of the prosthesis to be molded. The hardened investment material forming the mold cavity is porous to air.

Figure 6:
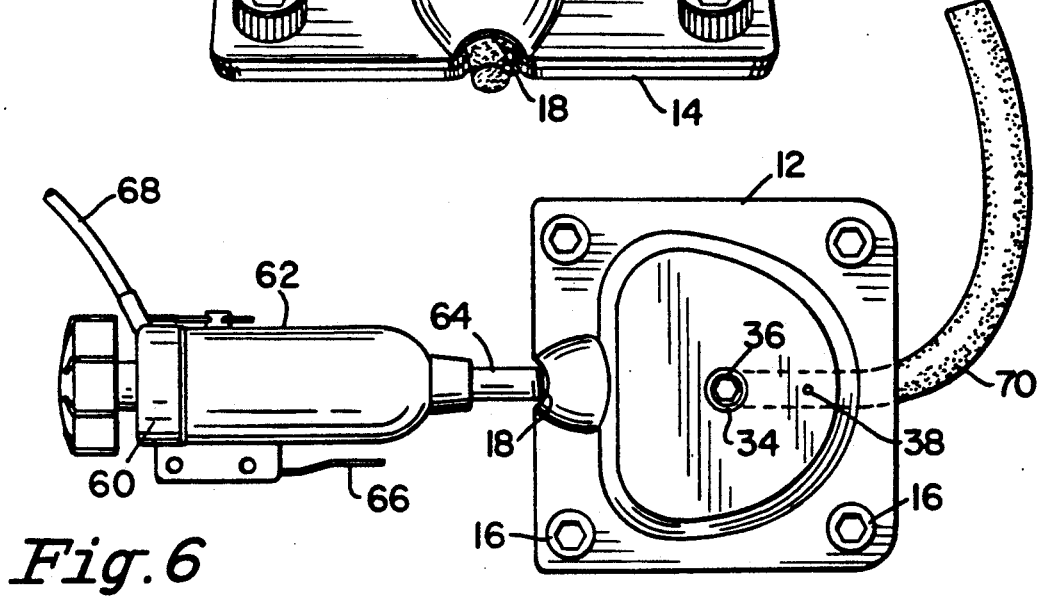
FIG. 6 is a top plan view of the mold shown in FIG. 1, with a mold material injector in position to inject molding material into the interior of the molding apparatus.

After the flask members have been reassembled, a relatively small, portable, hand-held injection device 60 (see FIG. 6) is threadedly connected with sprue opening 18 to inject into the investment mold cavity the molding material from which the prosthesis is made. The molding material preferably is an acrylic material, such as methyl methacrylate. Injection device 60 is a pneumatically-operated device that includes a material chamber 62, a material outlet tube 64, and a control lever 66. The device is connected through a pneumatic hose 68 to a source of pressurized air (not shown) by a conduit. When control lever 66 is depressed, air pressure is applied to the acrylic molding material within chamber 62 to force the molding material through outlet tube 64, through sprue opening 18 and into the cavity defined by the investment material. To assist in filling the cavity, a vacuum may be applied simultaneously through the porous investment mold to the cavity by way of a vacuum hose 70 connected to threaded opening 34a.

When the mold cavity has been filled with the molding material injection device 60 is removed from sprue opening 18, and a sprue closure screw 20 is threadedly installed in sprue opening 18, as shown in FIG. 1, to completely close the sprue opening. Packing pressure can be applied to the molding material within the investment mold cavity by threading closure screw 20 tightly into the sprue opening to exert pressure against the molding material contained within the sprue passageway and thereby ensure that the molding material will fully fill the investment mold cavity. As a result, sufficient material is forced into the cavity to fully form the prosthetic device and also to avoid shrinkage, so that the device will properly fit the mouth of the patient. Flask assembly 10 is then placed in heated water, or into a microwave oven, to apply heat to the molding material and permit it to cure to a solidified state. Cure times vary with the size and configuration of the prosthesis, as well as with the type of molding material that is used.

Figure 7:
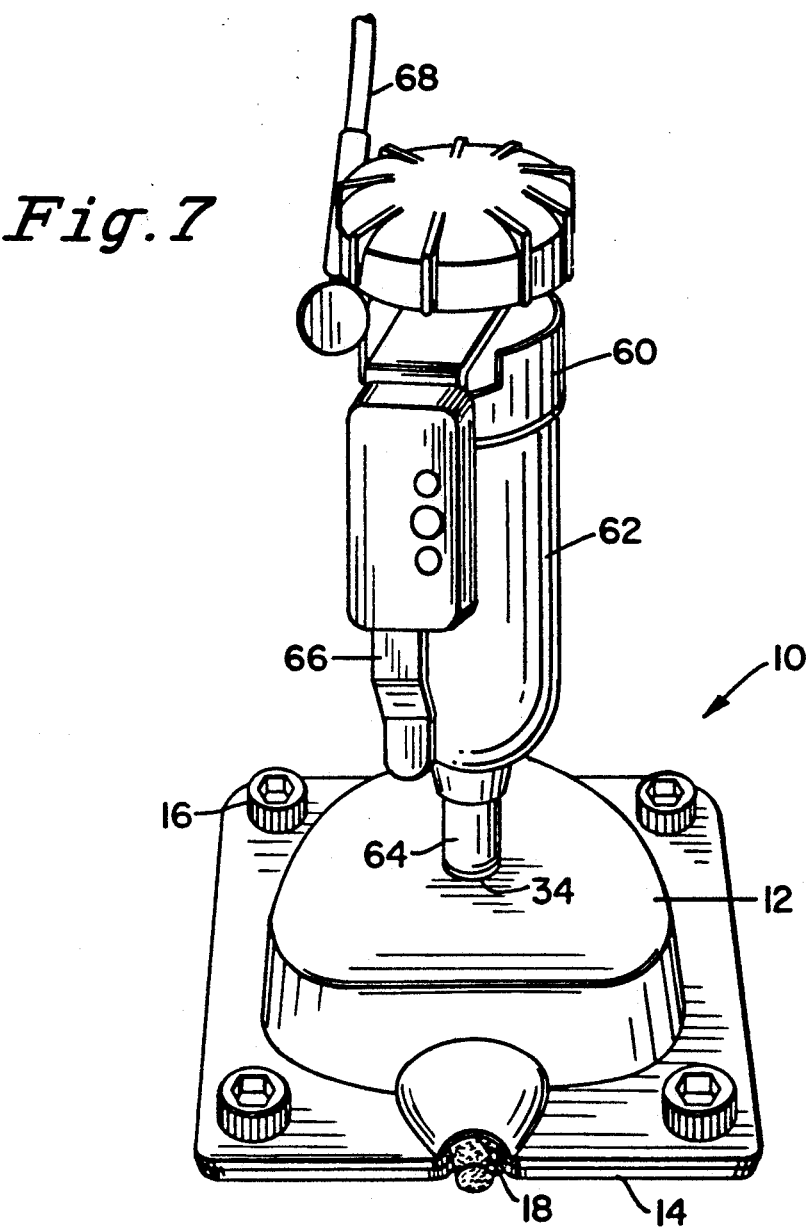
FIG. 7 is a top front perspective view of the molding apparatus shown in FIG. 1 with a pneumatically-operable injector in position to introduce pressurized air or gas against the investment material to effect mold separation to allow removal of the molded article.

After the molding material within the investment mold cavity has cured, flask assembly 10 can be opened by removing connecting bolts 16, and the completed prosthesis can be separated from the investment mold material and removed. To assist in separating the flask members after the connecting bolts have been removed, injection device 60 can be utilized to apply pressure against a portion of the investment mold, as shown in FIG. 7. Closure screw 36 is removed from upper flask member 12, and injection device 60 is threadedly connected thereto to permit the application of air pressure against the surface of the investment mold to facilitate separation of the investment mold from upper flask member 12. If necessary, the same separation technique can be utilized to separate the investment mold from lower flask member 14.

It has been found that the molding technique and the molding apparatus as herein disclosed provides high-quality molded prostheses, without the need for the trial packings that are characteristic in a number of the prior art devices. Consequently, unnecessary, repetitious, time-consuming procedures associated with trial packings can be eliminated, and the waste of material accompanying such trial packings can be avoided. Moreover, because the investing and injection of the prosthetic material is done in a closed flask, virtually all processing errors are eliminated, greatly simplifying the molding process.

Because the molding material is pneumatically injected, the injector can be loaded with cartridges containing the material, so that the material is not touched by the operator, and the risk of contamination is thereby minimized. Additionally, the operator is not subjected to the fumes and skin irritation that often accompanies handling raw methyl methacrylate, and because the injection is accomplished pneumatically, no physical exertion or estimation of the pressure necessary to be applied to the molding material is required. Finally, because the injection pressure is determined at the outset and regulated, the danger of applying excess pressure to the mold surfaces is avoided, and thereby the danger of mold surface damage caused by high pressures, sometimes referred to as "stone crush," is eliminated.

Because the flask forming part of the present invention is completely self-contained, external press structures to hold the investment mold members in position are not necessary, thereby reducing the capital costs involved in molding prosthetic products. Furthermore, the threaded openings in the top and bottom flask members facilitate separation of the flask members from the investment molds, and thereby eliminate the need for special separation tools.

Although particular embodiments of the present invention have been illustrated and described, it will be apparent to those skilled in the art that various changes and modifications can be made without departing from the spirit of the present invention. It is therefore intended to be encompassed within the appended claims all such changes and modifications that fall within the scope of the present invention.

What is claimed is:

1. Molding apparatus for molding a close tolerance part, such as a dental prosthesis, said apparatus comprising:
    a. a first mold member including a substantially planar first end face, a first cup-shaped recess in the first end face defining a first mold cavity portion, a first sprue recess formed in the first end face and extending from the first mold cavity portion to a first outer edge of the first mold member to define a first portion of a first molding material inlet passageway, a first threaded opening extending through the first mold member from the first mold cavity portion to define an investment material inlet passageway and for removably receiving a threaded closure member, at least one first vent recess formed in the first end face and extending outwardly from the first mold cavity portion to a second outer edge of the first mold member, wherein the first and second outer edges of the first mold member are spaced from each other;
    b. a second mold member including a substantially planar second end face, a second cup-shaped recess in the second end face defining a second mold cavity portion, a second sprue recess formed in the second end face and extending from the second mold cavity portion to a first outer edge of the second mold member to define a second portion of a first molding material inlet passageway, a second threaded opening extending through the second mold member from the second mold cavity portion for removably receiving a threaded closure member, at least one second vent recess formed in the second end face and extending outwardly from the second mold cavity portion to a second outer edge of the second mold member, wherein the first and second outer edges of the second mold member are spaced from each other;
    c. connection means for tightly holding the first and second mold members together in contacting relationship across their respective planar end faces so that said first and second mold cavity portions define a mold cavity, said first and second sprue recesses define a molding material inlet passageway extending outwardly from the mold cavity, and said first and second vent recesses define a vent extending outwardly from the mold cavity; and
    d. cooperating positioning means formed integrally with said first and second mold members to properly orient said mold members relative to each other as their respective planar end faces contact each other.

2. Molding apparatus in accordance with claim 1 wherein the molding material inlet passageway is of cylindrical cross section.

3. Molding apparatus in accordance with claim 2 wherein the molding material inlet passageway is internally threaded along a portion of its axial length to threadedly receive a closure screw for applying pressure on molding material contained within the mold cavity defined by the mold members.

4. Molding apparatus in accordance with claim 3 wherein the internal threads are adjacent an outermost portion of the molding material inlet passageway.

5. Molding apparatus in accordance with claim 3 wherein the molding material inlet passageway includes a cylindrical, unthreaded surface extending inwardly from the threaded portion to the mold cavity defined by the mold members.

6. Molding apparatus in accordance with claim 1 wherein the apparatus includes a portable, hand-held injection device for connection with the mold assembly through a molding material inlet passageway to inject molding material under pressure into the mold cavity.

7. Molding apparatus in accordance with claim 6 wherein the injection device is pneumatically operated.

8. Molding apparatus in accordance with claim 1 wherein the mold members are formed from a material that is transparent to the passage therethrough of microwaves.

9. Molding apparatus in accordance with claim 1 wherein said mold members are of generally rectangular configuration and the connection means includes a plurality of bolt members located at the corners of said mold members, each bolt member passing through a portion of one of said mold members and being received in a threaded opening formed in the other mold member.

10. Molding apparatus in accordance with claim 1 wherein the positioning means includes a plurality of spaced positioning recesses formed integrally on the end face of one of the mold members and a plurality of complementary positioning projections formed integrally on the end face of the other mold member, wherein the positioning projections are received in the positioning recesses to properly orient the mold members relative to each other.

* * * * *